United States Patent [19]

Fasnacht, Jr. et al.

[11] Patent Number: 4,868,798
[45] Date of Patent: Sep. 19, 1989

[54] CONTACT ULTRASONIC TRANSDUCER HEAD

[75] Inventors: Floyd A. Fasnacht, Jr., Forest; Michael G. Hacker, Rustburg; Orville L. Lindsey, Lynchburg; Thomas J. Smentek, Forest, all of Va.

[73] Assignee: The Babcock & Wilcox Company, New Orleans, La.

[21] Appl. No.: 273,667

[22] Filed: Nov. 18, 1988

Related U.S. Application Data

[63] Continuation of Ser. No. 43,672, Apr. 28, 1987, abandoned.

[51] Int. Cl.$^4$ ............................................. G01S 15/00
[52] U.S. Cl. ..................................... 367/104; 367/138; 367/7; 73/634
[58] Field of Search ...................... 367/95, 96, 99, 104, 367/173, 909, 137, 7; 376/249, 252; 73/633, 634, 641, 640

[56] References Cited

U.S. PATENT DOCUMENTS

| | | | |
|---|---|---|---|
| 3,988,922 | 11/1976 | Clark et al. | 376/249 |
| 4,158,309 | 6/1979 | Elsner et al. | 376/249 |
| 4,643,029 | 2/1987 | Klinvex | 376/252 |
| 4,681,730 | 7/1987 | Beuneche et al. | 376/252 |

Primary Examiner—Thomas H. Tarcza
Assistant Examiner—Daniel T. Pihulic
Attorney, Agent, or Firm—Robert J. Edwards; D. Neil LaHaye

[57] ABSTRACT

A contact ultrasonic transducer head assembly. A stationary housing is adapted to be fitted to a remotely operated manipulator. A movable assembly slidably received by the stationary housing has a plurality of independently suspended ultrasonic transducers mounted thereon. A position encoder mounted in the movable assembly monitors movement within the stationary housing. A limit switch is used to electrically disable the remotely operated manipulator when the movable assembly slides a predetermined distance into the stationary housing to prevent damage to the transducers or the surface being inspected.

8 Claims, 2 Drawing Sheets

CONTACT ULTRASONIC TRANSDUCER HEAD

This is a continuation of application Ser. No. 043,672 filed on Apr. 28, 1987 now abandoned.

BACKGROUND OF THE INVENTION

1. Field of the Invention

The present invention generally relates to ultrasonic inspection devices and in particular to inspection devices which are placed in direct contact with the work under inspection.

2. General Background

Ultrasonic examination of work such as pressurized water reactor vessels is typically performed from the inside of the vessel. During such examinations, ultrasonic transducers are manipulated by a remotely operated apparatus to scan predetermined areas of the reactor vessel. The examination is accomplished by generating an ultrasonic sound wave which is acoustically coupled to the vessel being inspected. The sound wave travels through the material of the vessel at a rate determined by the acoustic velocity of the material.

The acoustic velocity is a product of the material's density and elasticity. Reflections or echos of the sound wave occur whenever the velocity of the propagated sound wave is altered. The magnitude of the echo is related to the acoustic impedance of the reflecting material interface or, in the case of a flow, its size and orientation in relation to the size and orientation of the transmitted sound wave. Two methods of coupling the transmitted sound wave from the transducer to the vessel under inspection are generally used. In one, known as the immersion method, the transducer is submersed in water and placed a set distance, generally several inches, from the vessel wall. The sound waves are transmitted from the transducer, through the water, and into the vessel wall. Reflected sound waves are received by the transducer and electronically processed to determine the location of the reflection. A second method of inspection, the contact method, places the ultrasonic transducers in direct contact with the vessel under inspection. The sound is coupled to the vessel by a thin film of water. The transducer may be attached to a remotely operated manipulating system such as an automated reactor inspection system (ARIS) which controls the positioning of the transducer head inside the reactor vessel. As far as is known, previous applications of the contact method of inspection have involved the use of rigid plates specifically contoured for each geometric configuration examined in the vessel. A problem with this method is that several different plates would be required for a typical vessel inspection. Normally, the entire inspection tool must be removed from the vessel to change the inspection plate. Removal of the inspection tool to change out the inspection plate is impractical as such examinations are usually critical path. Ultrasound systems of which the inventors are aware include the following.

U.S. Pat. No. 4,489,729 entitled "Ultrasound Imaging System" is aimed at general applicatins for the medical field and discloses the use of a plurality of transducers, range signal means, timing means, energizing means for the transducers, means for listening for an ultrasonic wave, means for selecting a sequence of firing transducers, and means for producing an output representative of the received ultrasound signals.

U.S. Pat. No. 4,210,028 entitled "Method and Apparatus for Ultrasonically Measuring Concentrations of Stress" is aimed at vessel inspections and discloses an ultrasonic transducer array, means for measuring the time of flight of the acoustic waves within the object of interest, and means for determining from the time of flight measurements any variations in the acoustic velocity of the acoustic waves within the object of interest.

U.S. Pat. No. 4,096,755 entitled "Ultrasonic Inspection Apparatus" is aimed at inspection of aircraft fuselage components and discloses a carriage movable over a surface to be ultrasonically inspected, alternate transmitting and receiving ultrasonic transducers mounted on the carriage, means for causing each of the transmitting transducers to generate a burst of sound in the surface, separate detectors for each of the receiving transducers for detecting a shift in phase in the sound received by its associated receiving transducer due to a defect in the surface and for momentarily indicating a shift in phase indicative of a defect, a single master indicator for all transducers, and means for actuating the master indicator.

U.S. Pat. No. 4,252,022 entitled "Detection, Characterization and Studying of Flaws in Work by Acoustic Imaging" relates to acoustical holography and discloses a method of studying flaws in work having an irregular surface comprising generating and focusing acoustic energy on or near the irregular surface, scanning the surface with the focused acoustic energy, receiving resulting acoustic energy from echoes from flaws, and controlling the reception to reduce the effects of differences in the irregular surface.

U.S. Pat. No. 4,523,468 entitled "Phased Array Inspection of Cylindrical Objects" is aimed at pipe inspection and discloses a method of ultrasonically locating defects in an object with first and second transducer arrays comprising actuating at least one transducer of each array and causing the remaining transducers to assume a reflected receiving mode, measuring an ultrasonic wave travel time between transmission and receipt, determining the spatial relationship between the transmitting and receiving transducer, and determining the location of the defect from the measured travel time and relative spatial relationship of the transducers.

U.S. Pat. No. 4,604,897 entitled "Multitransducer Ultrasonic Transducer With Transducers of Different Sizes" discloses the use of probes of different sizes and control means for selectively activating successive groups of transducers.

U.S. Pat. No. 4,582,065 entitled "Ultrasonic Step Scanning Utilizing Unequally Spaced Curvilinear Transducer Array" discloses an assembly for use in a medical diagnostic system comprising a plurality of individual ultrasonic transducer elements and a mounting structure defining a curved array face for disposing the transducer elements in a convex curvilinear array.

The known art does not address the problem of variations in the water path distance in immersion testing. The use of several contact heads shaped to match the contour of the portion of the vessel under examination, a time consuming and impractical process, is also not addressed in the area of contact testing.

SUMMARY OF THE INVENTION

The present invention solves the aforementioned problem in a straightforward manner. What is provided is a contact head which holds a plurality of transducers.

The head assembly is mounted on a remotely operated tool capable of manipulating the head throughout a reactor vessel. Each transducer is fitted into an individual transducer holder and is mounted on an independent suspension system capable of contouring to irregular surfaces as well as conforming to surface contours ranging from flat to a thirteen inch radius. The transducers are contained in a larger transducer holder which is mounted on a movable assembly. The movable assembly is slidably mounted to a stationary housing which is mounted on a remotely operated tool. This movability gives the contact head the ability to stay in contact with the vessel wall during inspection regardless of minor geometric variations in the vessel. The movable assembly is provided with wear pads which support the load of the movable assembly against the reactor vessel wall. This allows the suspension system of the transducers to function independently and minimize wear on the transducers.

In view of the above, it is an object of the present invention to provide a contact head assembly with the ability to carry all transducers required to do a full reactor vessel inspection.

BRIEF DESCRIPTION OF THE DRAWINGS

For a further understanding of the nature and objects of the present invention, reference should be had to the following description, taken in conjunction with the accompanying drawings in which like parts are given like reference numerals and, wherein.

DETAILED DESCRIPTION OF THE PREFERRED EMBODIMENT

Figure 1:
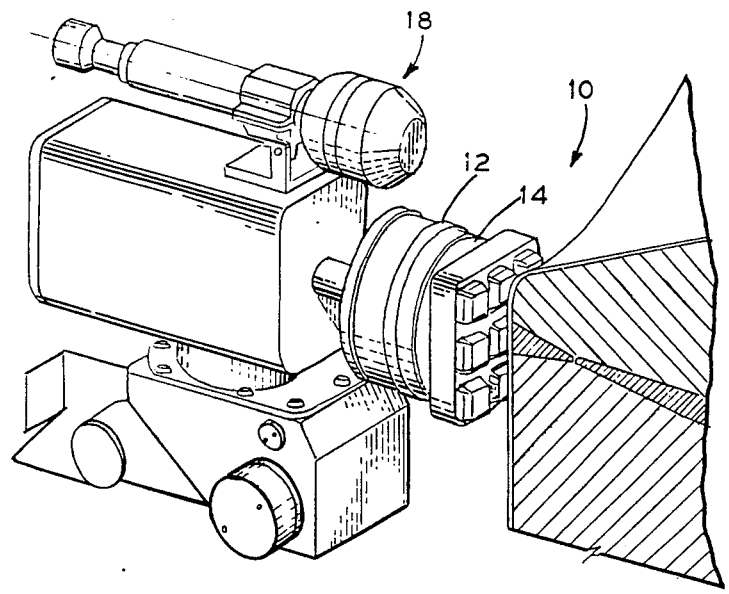
FIG. 1 illustrates the contact head assembly mounted on an ARIS manipulator.

Referring to the drawings, it is seen that the invention is generally referred to by the numeral 10. Contact ultrasonic transducer head 10 is generally comprised of stationary housing 12 and movable assembly 14.

Figure 2:
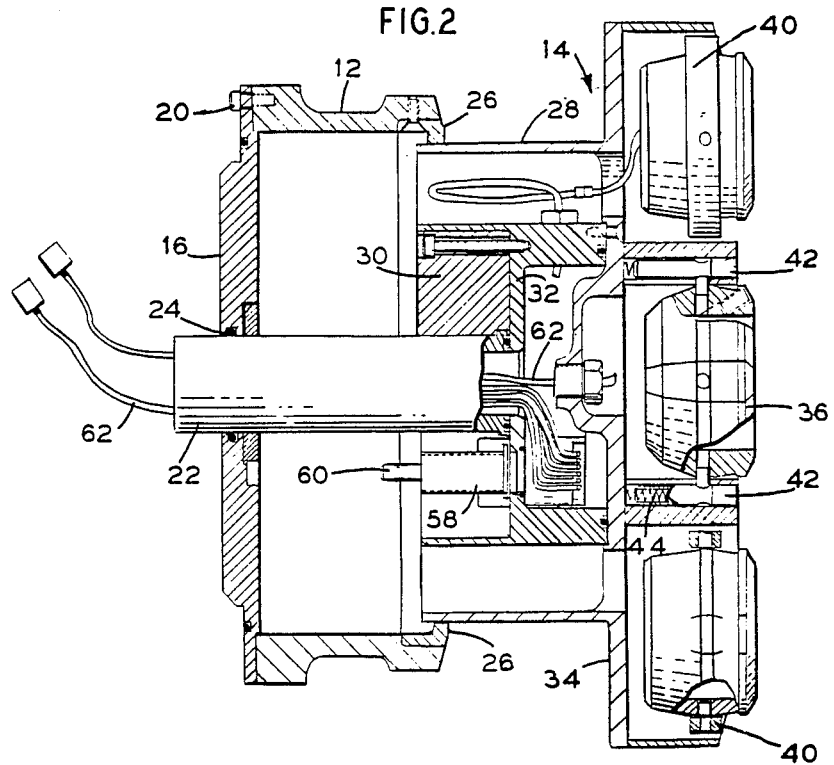
FIG. 2 illustrates a side sectional view of the contact head assembly.
Figure 3:
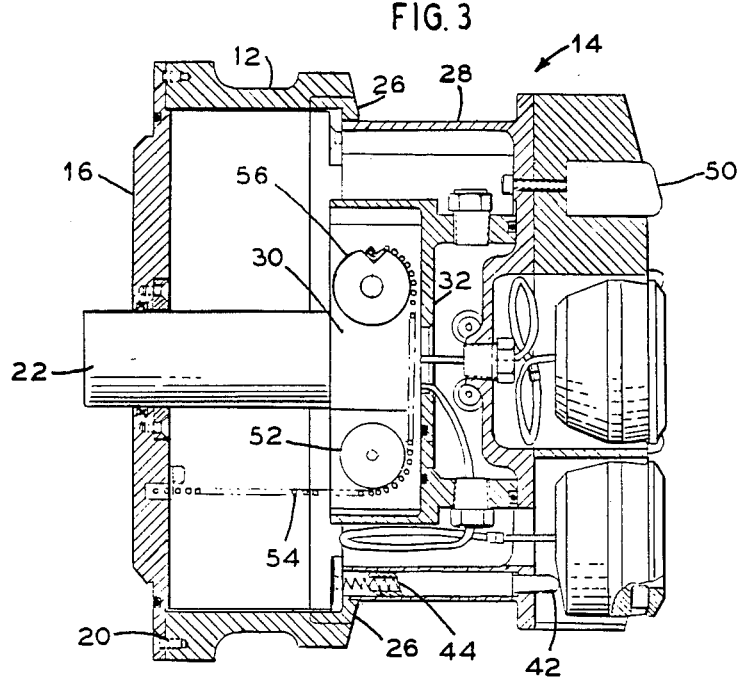
FIG. 3 illustrates a side sectional view of the contact head assembly rotated 45 degrees from the view of FIG. 2 and taken along the lines 3—3 of FIG. 4.

Stationary housing 12, best seen in FIG. 1-2, is adapted to be connected to a remotely operated tool by providing mounting plate 16 at the rear thereof. In the preferred embodiment, mounting plate 16 is adapted to be mounted to a manipulator such as the ARIS II or III manipulator 18 shown in FIG. 1. However, it should be understood that mounting plate 16 may be adapted to fit any suitable manipulator. As seen in Figure 1, stationary housing 12 is illustrated as being cylindrical and attached to mounting plate 16 by any conventional means such as screws 20. Mounting plate 16 is adapted to slidably receive tubular shaft 22 through which electrical connections to movable assembly 14 are run. Sealing means such as O-ring 24 may be used to prevent fluid leakage betwen mounting plate 16 and shaft 22. Transducer head assembly 10 may be mounted on ARIS manipulator 18 by extending shaft 22 into the manipulator and terminating it at the control system therein (not shown) where all electrical connections are made. With this direct connection to the control system, transducer head assembly 10 may be rotated 360 degrees by the manipulator to maintain proper alignment for complex vessel geometries. As seen in FIGS. 2 and 3, stationary housing 12 is provided with flange 26 around its forward internal edge which serves as a means of retaining movable assembly 14 within stationary housing 12.

Figure 4:
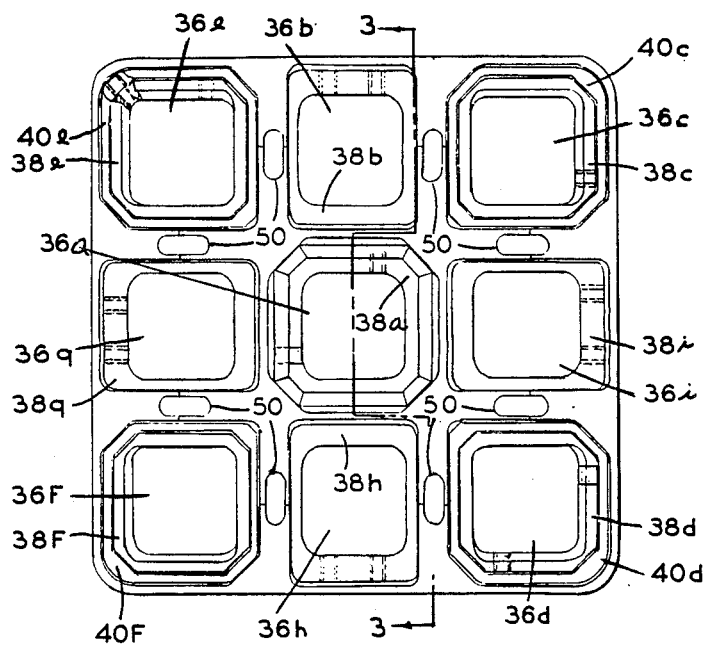
FIG. 4 illustrates a straight on view of the transducer array.

Movable assembly 14, seen in FIGS. 2 and 3, has its main body portion 28 sized to be slidably received within stationary housing 12 and is cylindrical in shape. Tubular shaft 22 extends through rear plate 30 and provides a path for electrical connections from ARIS manipulator 18 into transducer head assembly 10. Tubular shaft 22 terminates interior of movable assembly 14 and may be attached to interior plate 32 or formed integrally therewith. Transducder mounting plate 34 may be integral with interior plate 32 or attached thereto by any suitable means such as screws. In the preferred embodiment, transducer mounting plate 34 is adapted to receive nine (9) separate transducers. As shown in FIG. 4, transducers 36 are preferrably arranged in a 3×3 array. Each transducer 36 is fitted into an individual transducer holder 38. The four corner transducer holders 38 c, d, e, f are each mounted in corner transducer gimbals 40 c, d, e, f that allow the corner transducers 38 c, d, e, f to rotate on two separate axes independent of each other. Each corner transducer gimbal 40 c, d, e, f is held in place by two pistons (not shown) at a right angle to the gimbal to provide one of the rotational directions to the transducer. Each piston is loaded with a compression spring to allow movement of the transducer between its first normal flat position and second rotated position in response to movement across uneven surfaces. Side transducers 36 b, g, h, i are mounted in side transducer holders 38 b, g, h, i respectively that allow the respective side transducers to rotate on one axis. Each side transducer holder is held in place with two pistons which are spaced apart substantially 180 degrees around the transducer holder. Each piston is loaded with a compression spring to allow movement of the transducer between a first normal flat position and a second rotated position during movement across uneven surfaces. In addition, a plunger 42, seen in FIG. 3, is used to provide additional load distribution on each of side transducers 36 b, g, h, i. Each plunger 42 is biased toward its respective transducer by a spring 44. Center transducer 36a is mounted in center transducer holder 38a which is held in place by four pistons, one located at each corner of transducer holder 38a. Each piston is loaded with a compression spring to allow movement of center transducer 36a between a first flat position and second rotated position during movement across an uneven surface. This provides for rotation on two separate axes. Although each separate suspension system is not fully illustrated, pistons 46 and spring 48 are illustrative of the general arrangement of the transducer suspension system described above.

Transducer mounting plate 34 is provided with means for allowing the suspension system of the transducers to function independently of manipulator pressure on the surface being inspected and minimizing transducer wear. As seen in FIGS. 3 and 4, a plurality of wear pads 50, eight in the preferred embodiment, are attached to transducer mounting plate 34 by any conventional means such as screws. Wear pads 50 extend forward of transducer mounting plate 34 slightly less than transducers 36 to allow contact of the transducers with the surface being inspected while wear pads 50 continue to support the load of transducer head assembly 10.

Transducer head assembly 10 is provided with means for monitoring the extent of telescopic travel of movable assembly 14 within the stationary housing 12. As seen in FIG. 3, position encoder 52 is mounted in movable assembly 14. Chain 54 is anchored at its first end on mounting plate 16, engaged on a sprocket on position encoder 52, and anchored on its second end to take-up sprocket 56 which is spring loaded. Take-up sprocket 56 keeps chain 54 in tension so that any movement of movable assembly 14 within stationary housing 12 is detected by encoder 52 and relayed to the proper indicating means.

Means for electrically disabling the manipulator to prevent damage to transducer head assembly 10 or the surface being inspected as a result of excess pressure against the surface being inspected is also provided in the form of limit switch 58. Limit switch 58 is mounted in movable assembly 14 and has a plunger 60 which extends towards mounting plate 16. When movable assembly 14 slides completely into stationary housing 12, plunger 60 contacts mounting plate 16 and is forced into limit switch 58, which electrically disables manipulator 18 to prevent it from exerting excess pressure against the surface being inspected. Sliding of movable assembly 14 forward within stationary housing 12 may be accomplished by the use of pressurized air or hydraulic fluid supplied from manipulator 18. As seen in FIGS. 2 and 3, electrical connections to and from transducers 36, position encoder 52, and limit switch 58 are provided by wiring harness 62 which extends through tubular shaft 22 into manipulator 18.

In the preferred embodiment, mounting plate 16 has tubular shaft 22 extending therethrough for mounting on an ARIS II or III manipulator. However, the mounting plate and tubular shaft may be adapted to be mounted on any suitable manipulator. It is also pointed out that the transducer mounting arrangement allows for interchangeability of transducers and provides a minimum of a twenty-five (25) percent scan overlap for each transducer.

Because many varying and differing embodiments may be made within the scope of the inventive concept herein taught and because many modifications may be made in the embodiment herein detailed in accordance with the descriptive requirement of the law, it is to be understood that the details herein are to be interpreted as illustrative and not in a limiting sense.

What is claimed as invention is:

1. A contact ultrasonic transducer head assembly, comprising:
   a. a stationary housing;
   b. a movable assembly attached to said stationary housing for travel of said assembly within said housing;
   c. a transducer mounting plate attached to said movable assembly;
   d. a plurality of transducers in a 3×3 array mounted in said transducer mounting plate in an arrangement which provides an approximate minimum twenty-five percent scan overlap for each of said transducers; and
   e. a spring-loaded transducer suspension system attached to said transducer mounting plate and said transducers wherein each of said transducers is independently suspended to allow rotation on at least one axis between a first normally flat position and a second rotated position.

2. The assembly of claim 1, further comprising wear pads mounted in said transducer mounting plate.

3. The assembly of claim 1, further comprising means for monitoring the extent of travel of said movable assembly within said stationary housing.

4. The assembly of claim 1, further comprising a limit switch mounted in said movable assembly.

5. A contact ultrasonic transducer head assembly, comprising:
   a. a stationary housing;
   b. a movable assembly slidably attached to said stationary housing for travel of said assembly within said housing;
   c. a transducers mounting plate attached to said movable assembly;
   d. a plurality of transducers in a 3×3 array mounted in said transducer mounting plate in an arrangement which provides an approximate minimum twenty-five percent scan overlap for each of said transduces;
   e. a spring-loaded transducer suspension system attached to said transducer mounting plate and said transducers wherein each of said transducers is independently suspended to allow rotation on at least one axis between a first normally flat position and a second rotated position; and
   f. means for monitoring the extent of travel of said movable assembly within said stationary housing.

6. The assembly of claim 5 wherein said means for monitoring travel comprises a position encoder.

7. The assembly of claim 5, further comprising wear pads mounted in said transducer mounting plate.

8. The assembly of claim 5, further comprising a limit switch mounted in said movable assembly.

* * * * *